United States Patent [19]

Renirie

[11] 4,259,639

[45] Mar. 31, 1981

[54] CIRCUIT AND METHOD FOR DETECTING BATTERY SOURCE END OF LIFE

[75] Inventor: Alexis C. M. Renirie, Nijmegen, Netherlands

[73] Assignee: Vitatron Medical B.V., Dieren, Netherlands

[21] Appl. No.: 957,475

[22] Filed: Nov. 3, 1978

[51] Int. Cl.³ ............................................. G01N 27/42
[52] U.S. Cl. ...................................... 324/430; 324/426
[58] Field of Search ....................... 324/430, 426, 427; 128/419 PS

[56] References Cited

U.S. PATENT DOCUMENTS 4,031,899  6/1977  Renirie ............................ 128/419 PS

OTHER PUBLICATIONS

J. Geard et al, A Determination of the Internal Resistance of Leclanche-type Cells, Proceedings of the 4th International Symp on Batteries, Sep. 1964, pp. 219-230.

Primary Examiner—Michael J. Tokar
Attorney, Agent, or Firm—Woodcock, Washburn, Kurtz, Mackiewicz & Norris

[57] ABSTRACT

A circuit is disclosed for providing automatic detection of end of life of a battery source, particularly a lithium iodine type battery source characterized by a sharply increased internal resistance characteristic near end of life. The circuit periodically samples the short circuit output current of the source, the sampling being done at a high switching speed and for an extremely short time duration so that power consumption is minimized and only the resistive component which causes the knee in the resistance characteristic is measured. In the embodiment as incorporated in a cardiac pacer device, detection of the internal resistance knee is utilized to cause a step change in an operating characteristic of the pacer, such as stimulus rate, whereby end of life can be accurately monitored.

40 Claims, 8 Drawing Figures

CIRCUIT AND METHOD FOR DETECTING BATTERY SOURCE END OF LIFE

BACKGROUND OF THE INVENTION

1. Field of the Invention

This invention relates to circuits for monitoring the internal resistance of a power source, which power source is of the type having a changing internal resistance as a function of the energy depletion thereof and, more particularly, to a monitoring circuit for monitoring the internal resistance of a lithium type battery as used in an implantable pacer for determining pacer end of life.

2. Description of the Prior Art

Over the last several years, the lithium-iodine battery has been widely adopted as a power source for the pacemaker industry, as well as other applications. Indeed, the broad use of this battery system in the pacemaker industry has resulted in it becoming substantially the standard power source for that industry. Well over 100,000 such batteries have already been implanted, but the lifetime of such cells is great enough that the industry has not yet experienced the first occurrence where such a battery has come to end of life under nominal load and normal circumstances. For this reason, there is not yet any actual experience with the end-of-life (EOL) characteristics of the lithium-iodine cell. However, methods have been developed for approximately the EOL curve of such batteries, and it has become evident that there is a great need for matching, or interfacing, the device being powered by the battery with the parameters of battery behavior, in order to optimize EOL operation.

In the practice of the invention of this application, reference is made to "lithium systems", meaning lithium-type battery cells. As pointed out in the article of Parsonnet et al, American Heart Journal, October 1977, Vol. 94, No. 4, pp. 517–528, there are at least 5 types of lithium systems in widespread use today, including lithium iodine types such as made by Wilson Greatbatch, Ltd. and Catalyst Research Corporation. This invention is directed particularly, but withou limitation, to the lithium systems characterized by having an internal resistance characteristic curve which is substantially linear as a function of energy depletion until near EOL, at which time the characteristic exhibits a knee and internal resistance rises rapidly. This characteristic of lithium type sources is discussed in my U.S. Pat. No. 4,031,899, which patent is incorporated herein by reference. In the lithium iodine type battery, the cell cathode consists of molecular iodine weakly bonded to polyvinyl pyridine (P2VP). At beginning of life, there are about 6 molecules of iodine to each molecule of P2VP. No electrolyte as such is included in construction of the cell, but a lithium iodine (LiI) electrolyte layer forms during cell discharge, between the anode and cathode. The LiI layer presents an effective internal resistance to Li+ ions which travel through it. Since the LiI layer grows with the charge drawn from the battery, or milliamp hours (mAh), this component of the battery resistance increases linearly as a function of mAh (i.e., as a function of cell energy depletion). In the pacemaker environment, since there is constant energy depletion, this component of the internal resistance increases continually with time. However, particularly for a demand pacer which at any time may or may not be delivering stimulus pulses, the increase of this component is not linear with time, due to the fact that current drain is not constant.

For the lithium iodine type cell, there is another component of internal resistance which is caused by depletion of iodine in the cathode. The cathode is essentially a charge transfer complex of iodine and P2VP, and during discharge of the cell iodine is extracted from this complex. In the beginning there are about 6 molecules of iodine to each molecule of P2VP. During extraction of iodine from the complex the resistance to this procedure is low until the point is reached where about only 2 molecules of iodine are left for each molecule of P2VP, at which point this resistance rises very sharply. This gives rise to a non-linear internal resistance component which, for the lithium system, is called variously the depletion resistance, the depolarizer resistance, the charge transfer complex resistance, or the pyridine resistance. By whatever names, the combination of the non-linear component with the linear component produces the resistance characteristic with a knee occurring toward EOL, the knee being caused by the reaching of depletion of available charge carriers from the cathode.

Although EOL has not yet become a problem in the sense that implanted lithium pacers are still too young to have exhausted their lithium battery sources, the pacer industry has started to become aware of the potential problem of determining EOL. Since the internal resistance of the source rises drastically after the knee, the battery has very little useful lifetime left after the knee has been reached. Some pacer manufacturers have predicated their design for determining EOL upon detection of the battery output voltage, which voltage comprises the constant open circuit voltage minus the drop caused by the current drain across the internal resistance. However, this is a highly tenuous and very unsatisfactory premise for determining EOL, due to the fact that actual current drain near EOL cannot be predicted. For any manufacturer's pacer which is implanted, and used in combination with a given electrode, there will be a variation in the effective load as seen by the lithium battery, and a resulting variation in the overall current drain. Accordingly, if the EOL design is predicated upon sensing voltage drop to a given level, there can be very little assurance that the level chosen will correspond to the knee of the cell curve.

One lithium cell manufacturer, Catalyst Research Corporation, in a paper presented to the Workshop on Reliability Technology For Cardiac Pacemakers, October, 1977, pointed out that for such batteries sensing of the battery internal resistance is more reliable than voltage sensing. The position that cell resistance rather than cell voltage is a better warning indicator is based upon the observation that the resistance characteristic has a much less steep EOL curve. Stated differently, at low currents typical for pacers, plots of resistance against time give more warning than plots of voltage against time. If voltage characteristics for different current drains are plotted, the knees are observed to have a fairly wide variation, meaning that the voltage at which the knee might appear is subject to substantial variation as a function not only of the particular battery being used but also of the load being drawn by the pacer. On the other hand, plots of resistance indicate that the knee varies over a smaller range of values of internal resistance. Since the current drain may vary by as much as a factor of 2 due to different electrode loads, the variation in voltage may be twice as great as the variation of internal resistance. Monitoring the internal resistance provides a direct indication of the state of the battery, whereas monitoring the output voltage gives only a secondary indication, reflecting both the state of the battery and the operating condition of the pacer. This condition, it is anticipated, will be even more emphasized with the development of new, thin, large area cells which generally have steeper EOL slopes.

In my issued U.S. Pat. No. 4,031,899, there has been disclosed a circuit which can be programmed to provide an indication of the internal resistance of the lithium battery cell. As described in that patent, a switching circuit is utilized which alternately connects the relatively high current drain output circuitry and the relatively low current drain remainder of the circuit. By adjusting the duty cycle of the switching oscillator which controls the switching function, the voltage transferred from the battery to the respective circuits may be programmed to be substantially constant up until the resistance reaches the predicted value correspondingly to the knee of the curve, after which there is a programmed drop. Since the oscillator rate is linear as a function of delivered voltage, a programmed drop in frequency can be utilized to indicate that the battery resistance has reached the level where the knee was expected. This feature provides a decided advantage over EOL designs which sense voltage. However, the invention disclosed in this application has the added advantage that the exact resistance value at the knee need not be anticipated ahead of time. Even though the depletion resistance component is very predictable, the total value of the internal resistance at the time the knee is reached will be subject to some statistical variation so that EOL cannot be entirely accurately predicted by simply monitoring total battery internal resistance. What is acutely needed in the pacer industry, and provided for here, is circitry which accurately interfaces with the battery so as to make a highly reliable reading of the occurrence of the knee of the battery, along with means for providing an indication of the detection of such knee. The same need exists in other industries, such as electronic computers and space vehicles where batteries are utilized to maintain power during shut off of normal power, or in emergencies.

SUMMARY OF THE INVENTION

It is an object of this invention to provide an improved method and means for accurately detecting, even under worst-case conditions, the occurrence of the knee of the resistance characteristic of a battery source having a non-linear energy depletion characteristic.

It is another object of this invention to provide circuitry for interfacing with a lithium type battery source, which circuitry provides an accurate determination of the internal resistance knee of such battery.

It is another object of this invention to provide a circuit for use in combination with a lithium type battery source, which circuit has means for providing an accurate determination of the reaching of the non-linear depletion component of the battery internal resistance.

It is another object of this invention to provide for an improved pacer which utilizes a lithium type battery, which pacer includes a circuit which interfaces with such lithium battery to provide an accurate indication of battery end of life even under worst case conditions.

It is another object of this invention to provide a means for accurately determining the onset of increased resistance in a lithium battery system which occurs due to depletion of iodine in the system cathode.

It is another object of this invention to provide a circuit which interfaces with a lithium battery, which circuit is of low power drain and provides for substantially continuous monitoring of the internal resistance of such battery to determine when such battery is at about the knee of its internal resistance characteristic.

It is another object of this invention to provide a device comprising a lithium type battery source and a circuit for providing desired output signals, in combination with a circuit which provides a reliable indication, substantially independent of the load drawn by such output circuit, of the end of life characteristic of such battery.

It is another object of this invention to provide a method for measuring only the depletion resistance component of a lithium type battery, such method effectively distinguishing the depletion component from the linear resistance component.

In accordance with the above objects, there is provided a circuit, particularly adapted for use in an implantable pacer, but likewise adaptable for use in a wide variety of other applications, which circuit interfaces with a battery source having an internal resistance characteristic which is substantially linear over most of its lifetime and which, near end of life, reaches a knee following which said internal resistance rises sharply. The circuit is adapted to measure that component of the internal resistance which causes the knee in the internal resistance characteristic, and to provide an output useful for control of the device being driven by the battery, so as to provide an end of life indication. In the preferred embodiment a high speed switching circuit is provided for measuring short circuit current drain from the battery over a small time duration, so that such short circuit current reflects substantially only the depletion component of the resistance which causes the knee, and does not reflect the linearly increasing internal resistance component. The circuit utilizes the fact that the electrical representation of the battery source comprises the linearly increasing resistance component in parallel with an effective capacitance, such that for very short samples of short circuit current from the battery the linear component is shunted. By comparing the sampled short circuit with a predetermined value corresponding to a given level of the depletion resistance, which level is selected to clearly indicate the knee of the resistance characteristic, there is obtained an unambiguous indication that the battery is near end of life.

DESCRIPTION OF THE PREFERRED EMBODIMENTS

In this specification, reference is made particularly to the lithium-iodine cell as manufactured by Catalyst Research Corporation, Baltimore, Maryland. The term "lithium-type" as used herein refers to the lithium iodine battery as well as other lithium systems such as those disclosed in the aforementioned article of Parsonnet et al. More broadly, the term "lithium-type" refers to a battery or cell having approximately the characteristics displayed by the lithium iodine battery. The salient features of these characteristics are shown by the equivalent circuit within the dashed block 30 of FIG. 1. The cell has an effective open circuit voltage $E_o$ which, by way of illustration, is about 2.8 volts for the Catalyst Research battery. The effective internal impedance in series with $E_o$ comprises 2 resistance components. The first resistance component, shown as $R_L$, represents the resistance to the travel of Li+ ions through the LiI layer. This resistance is a direct linear function of the charge or energy drawn from the battery, such that this component is linear as a function of battery usage. In the curves shown in FIG. 2A and FIG. 2B, usage is plotted in millilamp hours (mAh). In FIG. 2A, it is seen that for a typical worst case analysis of a lithium type battery, for a 15 uA load, this component of the resistance is less than 10 K ohm at about 2,000 mAh. However, statistically this will vary, and as shown for the worst case high characteristic, 15 uA load, such internal resistance component could be on the order of 15 K ohm. FIG. 2A also shows $R_L$ as a function of mAh for the 25 uA typical case, illustrating that the rate of increase will vary with the load current. The fact that $R_L$ is higher at 15 uA current drain than at 25 is explained by the fact that at lower rates of discharge a more perfect crystal lattice is formed which slows down the passage of the Li+ ions.

Figure 1:
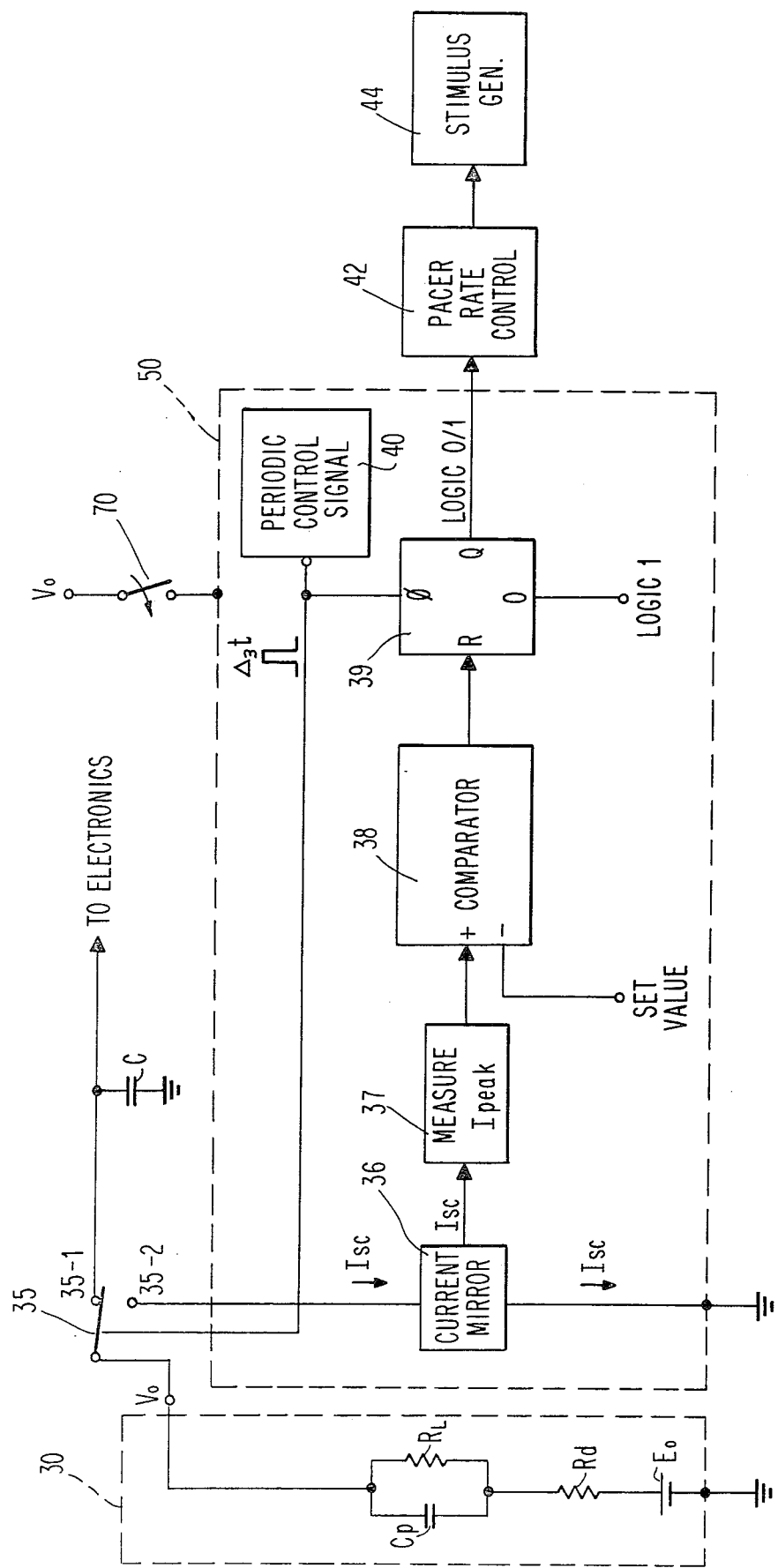
FIG. 1 is a diagram of the battery source and the circuitry comprising this invention, showing the interfacing of the circuitry with the battery source.
Figure 2A:
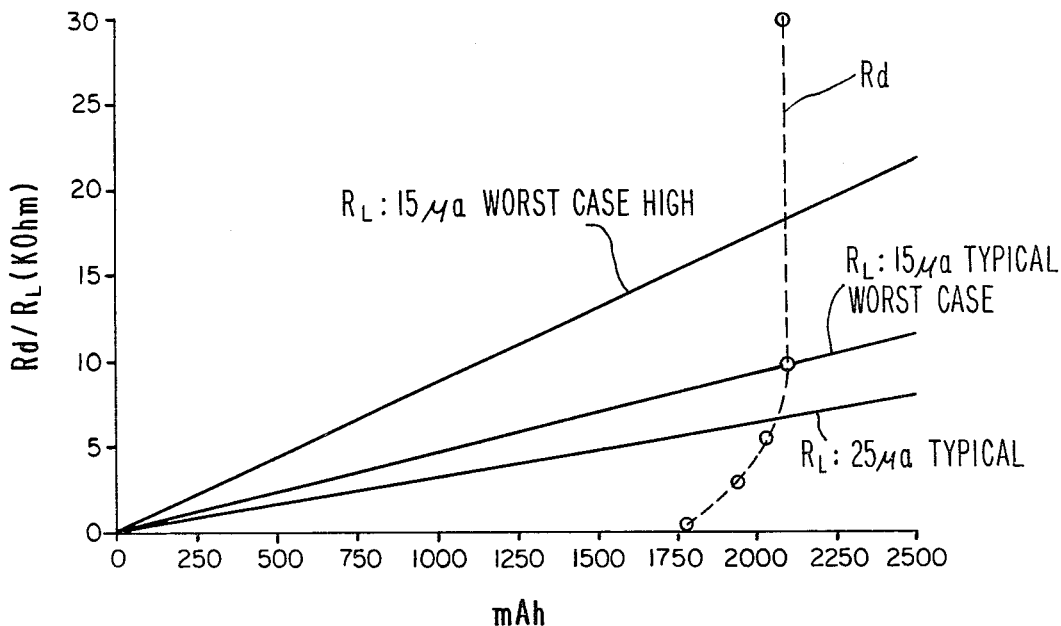
FIG. 2A is a set of curves illustrating the variation of the components of battery source internal resistance as a function of total battery use, or energy depletion.

In practice, it is found that $R_L$ is effectively shunted by a capacitance shown in FIG. 1 as $C_p$. This capacitance is typically about 0.2 uf at beginning of life, and the parallel combination of electrolyte resistance and capacitance has been found to have a relatively steady time constant in the range of about 40 to 60 microseconds. Accordingly, signal frequencies of 1 megahertz, or pulses of time duration of 1 microsecond or less, are effectively passed right through the combination were a short circuit. Even for pulses of a time duration of about 10 u seconds, the electrolyte capacitance provides a substantial short circuit.

Figure 2B:
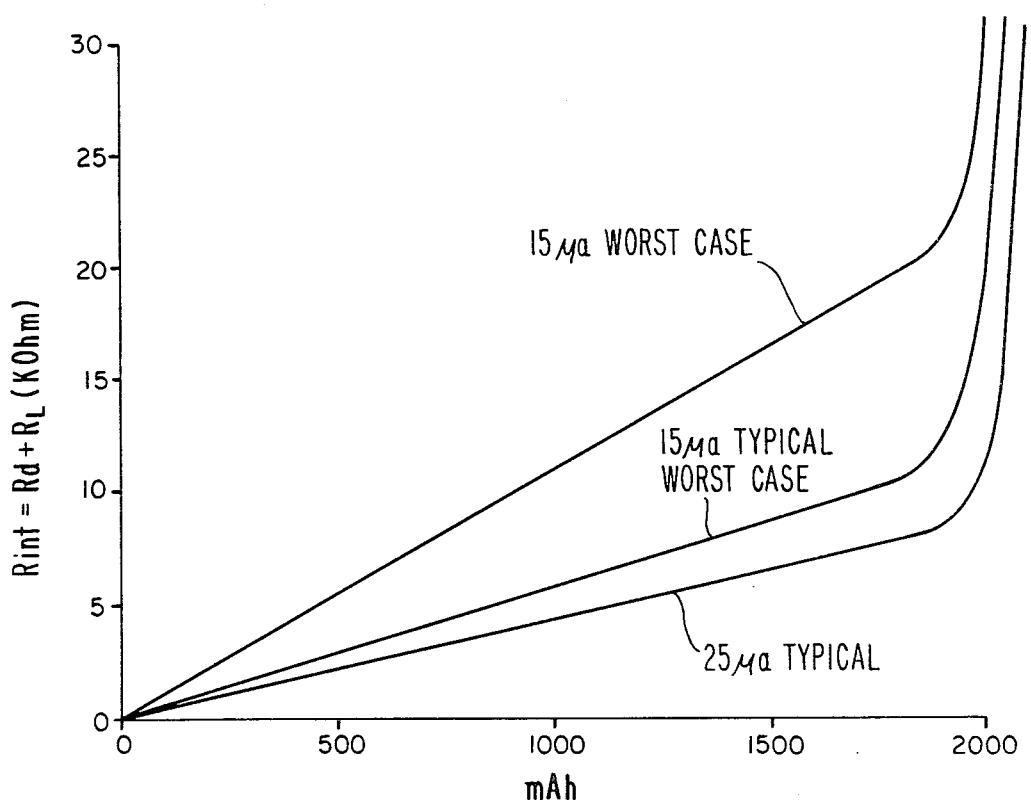
FIG. 2B is a set of curves showing the combined internal resistance of the battery source as a function of use.

The second resistance component, as seen within dashed block 30, is represented by the designation $R_d$. This resistance is referred to as the depletion resistance, and represents a resistance component that increases rapidly at EOL due to depletion of iodine in the cathode. It commences at substantially the same total usage regardless of what the operating load has been. As seen in FIG. 2A, this resistance component is negligible until a certain usage, which for the battery illustrated is about 1750 mAh. Thereafter, the depolarizer or depletion resistance component rises sharply, and becomes the determinant of EOL. For the example shown, from the point where the depolarizer resistance is first significant, until the curve becomes substantially vertical, the battery has approximately 400 mAh of useful life remaining. As seen in FIG. 2B, where total internal resistance is plotted as a function of usage, the effect of $R_d$ soon swamps the effect of the linear component $R_L$, causing EOL.

The above observations of the internal electrical characteristics of the lithium type source provides the basis for the means of detection utilized by this invention. While there apparently is some small capacitance associated with the depletion component, this is negligible even at frequencies much higher than 1 MHz. Accordingly, pulse signals with a duration of about 1 us, either from or into the lithium source, are affected by the depletion resistance component but not by the linear resistance component. Such small time duration signal can thus be used to determine when $R_d$ has begun to rise from a negligible to a significant value, indicating that the knee of the source curve has been reached.

It is to be noted that the curves shown in FIG. 2A and FIG. 2B are representative, and are simplifications to a certain degree. Certain observations have been made and published to the effect that there are non-linear portions of the resistance characteristic curves at beginning of life. For purposes of this invention, such other non-linearities are not important and accordingly are not treated. When reference is made to the linear portion of the resistance characteristic, this means the substantially linear build-up of resistance which characterizes most of the lifetime of the battery source, whereas the non-linear component represents the EOL sharp increase in resistance which, for the lithium iodine cell, is caused by the increase of depolarizer resistivity due to iodine depletion.

Still referring to FIG. 1, there is shown a block diagram of a circuit which interfaces with the battery in a manner such as to make an accurate determination of when $R_d$ begins to increase, and therefore when the knee of the resistance characteristic has been reached. The term "reached" in this context means that the battery usage is such that operation on the knee of the curve has commenced. The battery 30 may have one terminal grounded, as shown, and the other terminal is connected through switch 35 to the electronics of the device being powered by the battery. A capacitor C is shown, which stores energy delivered from the battery, to provide a smooth and constant flow of current to the electronic circitry. For the use of this invention in a pacemaker embodiment, the electronics includes the stimulus generator 44 and pacer rate control circuitry 42, as shown, as well as other amplifier and logic circuitry common to pacers.

Switch 35 is suitably periodically switched by periodic control signal generator 40, which provides a very short time duration switching signal designated $\Delta_3 t$.

The value of $\Delta_3 t$ is chosen small enough so that no appreciable change in the charge on capacitor $C_p$ is possible during the time that switch 35 is disconnected from the electronics and connected to node 35-2. When switch 35 connects the battery between node 35-2 and the ground, the battery is presented with an effective short circuit, as indicated by the current designation $I_{sc}$. Circuit 36 provides such effective short circuit between node 35-2 and ground, and also includes a current mirror which provides an output which is substantially equal to $I_{sc}$. Current mirror designs possessing these circuit characteristics are widely known and are used in many applications. This current, which exists only for the short time period of $\Delta_3 t$, is connected to circuit 37 which measures the peak current flowing during that time period. The output of the peak measuring circuit 37 is connected to one terminal of comparator circuit 38, the other terminal being connected to a reference or set value, against which the measured peak current is compared. The set value is predetermined to correspond to a peak short circuit current derived from the battery which in turn corresponds to a predetermined value of $R_d$, such value being suitably 1K, 5K, or 10K, the exact value being a matter of design choice. The ruling criterion for determining the set value is that it corresponds to a value of $R_d$ which is high enough to indicate that $R_d$ has commenced to increase, thereby indicating that the knee of the resistance characteristic has been reached. Until the knee has been reached, the output of circuit 38 will be of a first value, such that a reset signal is continuously produced and connected to the reset terminal of D type flip-flop 39. However, when the value of $R_d$ has increased to a point equal to or greater than that corresponding to the set value, no reset signal is generated, and upon each output from the periodic control signal generator 40 a logic signal 1 is communicated through to pacer rate control circuit 42. Pacer rate control 42 is any conventional circuit adapted to change the rate of outputting stimulus pulses from the pacer stimulus generator 44.

It is observed that an important condition for opration of the circuit as shown in FIG. 1 is that $\Delta_3 t$ must be small enough so that the effective capacitance $C_p$ is an effective short circuit during the time period $\Delta_3 t$. This being the case, $R_L$ is effectively shunted, and the short circuit current is a function substantially only of the battery output voltage $E_o$ and the non-linear (or depolarizer) resistance component, $R_d$. To the extent that the current mirror circuit 36 is not an absolute short circuit between node 35-2 and ground, the value of the resistance in that path may be compensated for by standard compensating circuitry in either the current peak measuring circuit 37 or at the comparator 38. Indeed, the current mirror may be designed with a predetermined input resistance, in order to minimize current drain.

The periodic control signal, indicated in FIG. 1 by block 40, may be provided by the circuit disclosed in my issued U.S. Pat. No. 4,031,899, assigned to the same assignee. In that circuit, there is disclosed a switching circuit, connected to and powered by the battery source, which alternatively connects the battery source to a high load circuit and a low load circuit. The disclosure of that patent provides that both the frequency and the duty cycle of the switching circuit may be varied. Accordingly, that circuit may be adopted for use in this invention, adjusting the duty cycle so that the battery is connected through the switching circuit to node 35-1 for most of the time period of the switching cycle, and to node 35-2 for a determined interval $\Delta_3 t$ which is chosen to be small enough so that $C_p$ remains an effective short circuit during such time period.

Figure 3A:
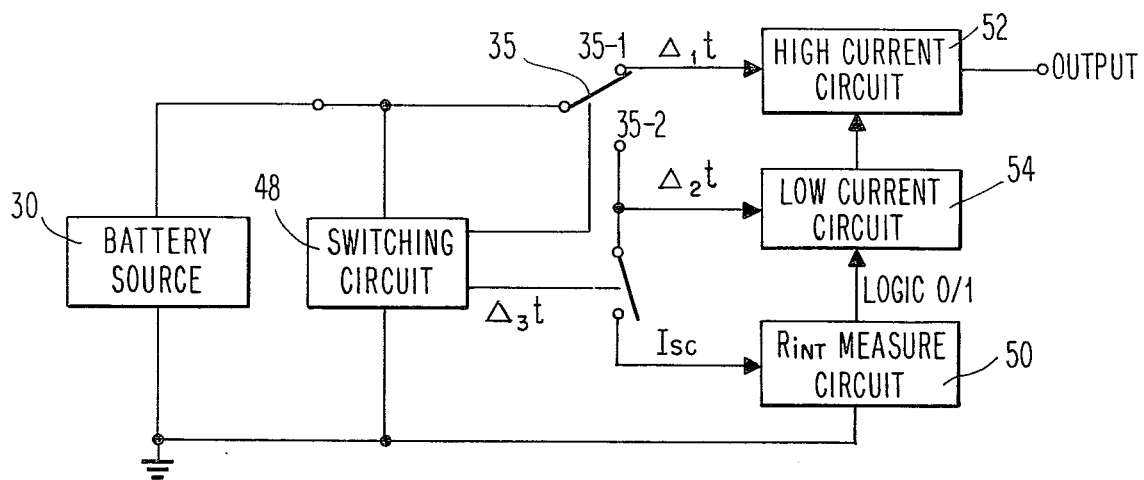
FIG. 3A is a block diagram showing an embodiment of the invention wherein the sampled current, which is reflective of the depletion resistance component of the battery source, is obtained while the battery is connected only to a low current portion of the circuit which it is powering.
Figure 3B:
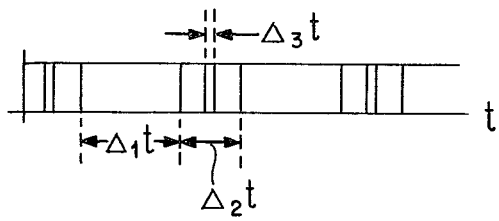
FIG. 3B is a diagram showing time relationship of the periods when the different circuits are connected to the battery source in the circuit of FIG. 3A.

Referring to FIG. 3A, the switching circuit of said U.S. Pat. No. 4,031,899 is shown as circuit 48, providing switching means for switching the battery terminal between mnodes 35-1 and 35-2. In the arrangement of FIG. 3A, for a first time period $\Delta_1 t$, the battery is connected to a high current circuit 52. For a second period of time $\Delta_2 t$, the battery is connected across a low current circuit 54. In the pacer embodiment, such low current circuit 54 generates trigger pulses which are communicated to the high current output circuit 52, which latter circuit provides the stimulus pulses which are communicated to the patient's heart. For the arrangement of FIG. 3A, the switching circuit may also suitably generate a separate small measuring time interval $\Delta_3 t$ during the interval $\Delta_2 t$, as illustrated at switch 45 and in FIG. 3B. In this arrangement, the low current circuit 54 is connected to the battery while the circuit for measuring internal resistance is connected across the battery, but this introduces very little error into the measurement. The low current circuit of a typical pacer as made by the assignee of this application draws only about 2.5 uA, whereas the peak short circuit current through circuit 50 is on the order of 1 ma or higher. Accordingly, negligible distortion in the measuring is suffered by this circuit.

Figure 4A:
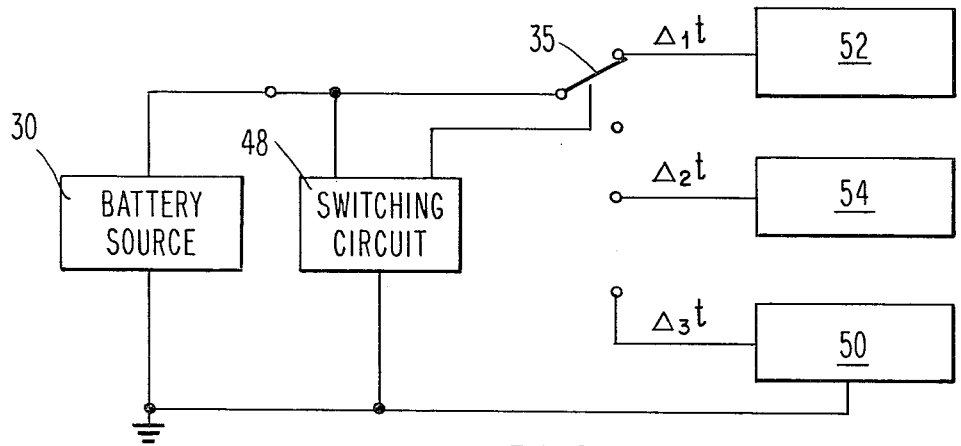
FIG. 4A is a block diagram showing an alternate embodiment of the invention, wherein the circuit for measuring the depletion component of the battery source internal resistance is switched across the battery source for a time duration while the battery is not connected to any other load.
Figure 4B:
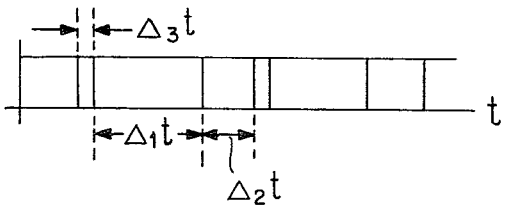
FIG. 4B is a diagram showing the time relationship of the periods during which the different circuits of the device are connected to the battery source, for the circuit of FIG. 4A.

FIG. 4A, and accompanying diagram FIG. 4B, illustrate an alternate technique for isolating the measuring circuit 50 from both the high current circuit 52 and the low current circuit 54. In this arrangement, the switching circuit 48 produces 3 distinct time periods, namely $\Delta_1 t$ during which power is supplied to the high current circuit; $\Delta_2 t$ during which power is supplied to the low current circuit; and $\Delta_3 t$ during which the measurement of the battery internal impedance is made. By this switching arrangement, the measuring circuit, when enabled by switch 35, is isolated from and independent of any loading effect of either circuit 52 or 54.

In order to conserve battery power, the measuring circuit 50 may be connected to the battery output through a normally open switch 70, such as a magnetic reed switch. After a certain safe period of time, e.g., 5 years for a pacer, the switch could be closed by an external programming signal. For an example of such external program means, see the copending application of this assignee, U.S. Ser. No. 805,037 now issued as U.S. Pat. No. 4,120,031.

Figure 5:
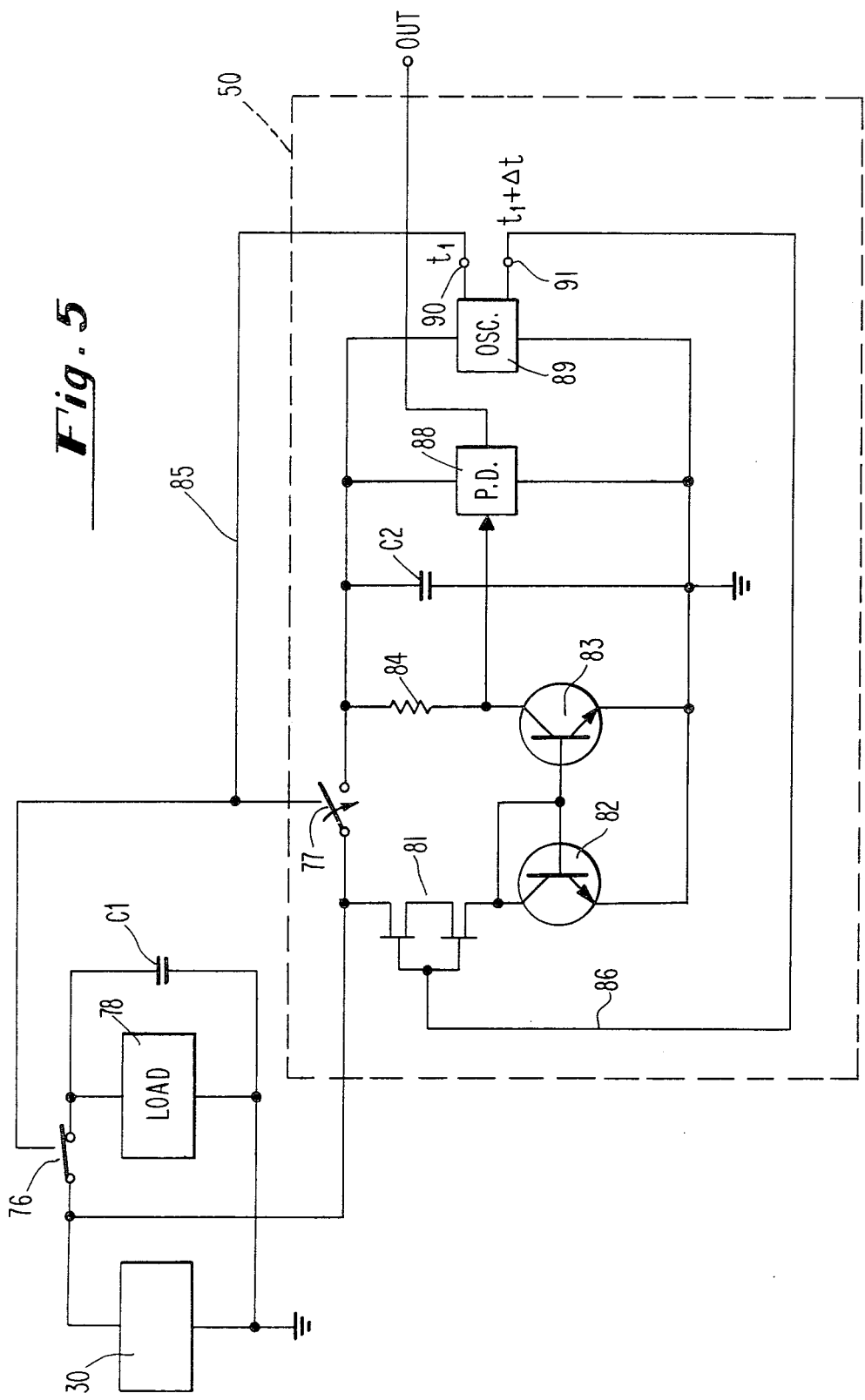
FIG. 5 is a circuit diagram of a specific embodiment of the invention.

Referring now to FIG. 5, there is shown a specific circuit diagram of a preferred embodiment. Battery 30 normally drives a load 78 through normally closed switch 76. A storage capacitor C1 is tied across load 78. Detector circuit 50 is normally disconnected from battery power through switch 77. Switches 76 and 77 may be conventional FET devices. Detector circuit 50 comprises a CMOS pair 81 comprising two inverters of the low $V_p$ type ($V_p$ equals approximately 0.7 volt-1 volt). The CMOS pair conducts only at the time of switching, as is well known, which occurs only when the proper switching signal is placed on line 86. CMOS pair 81 is connected to the collector of transistor 82 which has its collector also tied to its base. Transistors 82 and 83 are combined in a current mirror configuration, with resistor 84 connected to the collector of transistor 83. Storage capacitor C2 is tied between switch 77 and ground, as is peak detector 88 and oscillator 89. Oscillator 89 can be adjusted to have any suitable rate and any desired duty cycle. A periodic signal is outputted from node 90 to line 85, to control the switching of switches 76 and 77. Thus, at time $t_1$, switch 76 may be switched open while switch 77 is switched closed, such that power is delivered through switch 77 during the time that power is disconnected from load 78. The oscillator output at node 91 is connected by line 86 to the input of CMOS pair 81. The output at node 91 occurs at time $t_1 + \Delta t$, providing a small time delay which is shorter than the length of the switching signal at node 90. The time delay may be provided, for example, by adjusting the duty cycle of the oscillator appropriately and outputting the negative signal at node 91 relative to node 90, or a separate conventional delay circuit may be utilized within oscillator block 89.

In operation, load 78 is normally connected through switch 76 to battery source 30. At the time of switching at oscillator 89, a switching signal is delivered on line 85 which opens switch 76 and closes switch 77. At that moment, and for the duration of the switching signal on line 85, the load is disconnected from the battery and all circuit portions of detector circuit 50 are connected to the battery source. Note that oscillator 89 continues to operate even when switch 77 is open, due to the energy stored in capacitor C2. At time $t_1 + \Delta t$, CMOS pair 81 switches. As is well known, the switching time of a CMOS pair is extremely short, and current flows through the pair only at the time of switching. Pair 81 is connected between the battery source and ground through transistor 82, providing an effective short circuit across battery 30 during the CMOS switching time. The short circuit current is generated through resistor 84, typically of a value of 500 ohms, due to the current mirror action of transistors 82 and 83. The change in voltage across resistor 84 due to the short circuit current is developed at the collector of transistor 83 and inputted to peak detector 88. The output of peak detector circuit 88 is provided as an indication of whether the battery short circuit current is above or below a predetermined level corresponding to the point where the depletion resistance is deemed to be of such value that the knee has been reached. It is preferable that the peak detector provide positive monitoring i.e., give an output pulse for each switching cycle as long as the battery has not yet reached the knee. Negative monitoring would constitute providing output pulses only when the knee has been reached, indicating end of life. The advantage of positive monitoring is that information is provided both that the battery has not yet reached the knee and that the test circuit is working. The test circuit of FIG. 5, operating at a voltage of 2.8 volts, draws only about 1 microamp of current.

It is thus seen that there is disclosed a circuit useful for making a high accuracy measurement of the non-linear or depolarizer component of the internal resistance of a lithium type battery source. The circuit acts upon the principle of providing a very short time duration appreciable short circuit across the battery, so that the current flowing into and through the measuring circuit is appreciably a factor only of the open circuit voltage of the battery source and the non-linear component of the battery internal resistance. The measurement of the non-linear portion, designated in FIG. 1 as $R_d$, constitutes a measurement of the knee component of the total internal resistance characteristic, thereby providing a means for accurately detecting when the battery has reached the knee of its characteristic. As used herein, the circuit is adaptable for providing a control signal useful for controlling the performance of the circuit being powered by the battery source. While the preferred embodiment has been described in terms of a pacemaker, it is to be noted that the invention is equally adaptable to any type of device which is powered by a lithium-type battery source.

As used in claiming this invention, the terms "appreciable short circuit" and "substantial short circuit" denote a low resistance path, but one which may have a finite resistance. As has been pointed out, the sampling circuit placed across the source during the short sampling period may present a predetermined resistance load. Indeed, the depletion resistance component may be measured, for example, by designing the sampling resistance to be equal to the value of $R_d$ considered to represent beginning of EOL, e.g., 1K or 5K. For this arrangement, the voltage across the source output terminals is compared with a reference, it being known that when $V_o$ sampled has dropped to one-half of $E_o$, or 1.4 volts, that $R_d$ has increased to the predetermined value of the sampling resistance. The critical feature, then, is not the precise form of the measuring circuit, but in achieving a quick enough sampling time that the effect of $R_L$ is not measured. During such sampling time, either source output variable (current or voltage) may be monitored to derive the EOL signal. Of course, if source output voltage is measured, the measuring circuit must be isolated from any other circuit to a high degree, so that the source drives substantially only the predetermined loading of the measuring circuit.

In another embodiment of the invention, more suitable for applications where an external power supply is available (but also adaptable to a pacer system), the measuring circuit 50 is altered to contain a high frequency generator. During the sampling period, the circuit delivers a voltage regulated pulse to the source, and the circuit measures the resulting current which is a function of the depletion resistance. In this arrangement, the measuring, or detector circuit may be permanently constructed together with the load circuit, or it may be connected separately whenever testing of the source is desired. But in either event, the basic requirement is to switch the detector circuit sufficiently quickly that the electrolyte capacitance shunts the linear resistance $R_L$ so as to prevent it from having any effect on the measurement of internal resistance. For one of ordinary skill in this art, the receiving and generating embodiments of the detector circuit are equivalents in the practice of this invention.

I claim:

1. A self monitoring power source, having a battery source having a resistance-use characteristic with a linear component which increases substantially linearly with battery usage and a non-linear component which increases sharply after a certain usage, said characteristic having a knee caused by said non-linear component, in combination with detecting means connected to said battery source for detecting the occurrence of said knee and providing a signal indicating that said knee has occurred.

2. The power source as described in claim 1, wherein said detecting means detects the increase of said non-linear component to a predetermined value.

3. The power source as described in claim 1, wherein said detecting means detects the increase of said non-linear component to a predetermined level relative to said linear component.

4. The power source as described in claim 1, comprising a load output for connection to a load, and switching means for switchably isolating said detecting means from said load output.

5. The power source as described in claim 4, wherein said switching means isolates said load output from said source while said detecting means is in operative connection with said source.

6. The power source as described in claim 1, wherein said detecting means comprises a CMOS pair connected to said battery source, and means for periodically switching said CMOS pair.

7. The power source as described in claim 6, comprising a current mirror circuit connected to said CMOS pair for providing a measurable current substantially equivalent to the current through said CMOS pair.

8. The power source as described in claim 1, wherein said detecting means comprises means for providing a two-state output, one of said states indicating said knee has not occurred and the other indicating that said knee has occurred.

9. The power source as described in claim 1, wherein said detecting means detects when said non-linear component has increased to about a predetermined level.

10. The power source as described in claim 9, wherein said detecting means places an appreciable short circuit across said source for a predetermined short sampling period, and has means for measuring the resulting current from said source.

11. The power source as described in claim 10, wherein said linear component is effectively shunted by a capacitance component, and said sampling period is sufficiently short so that said linear component is effectively shunted during said sampling period, whereby said resulting current is representative of said non-linear component.

12. The power source as described in claim 4, wherein said detecting means comprises means for measuring substantially the current delivered by said source while it is in operative connection therewith.

13. The power source as described in claim 12, wherein said detecting means provides an effective short circuit to said source while in said operative connection.

14. The power source as described in claim 13, wherein said linear component is shunted by an effective capacitance, and said operative connection is of a time period limited so that said linear component is effectively short circuited during said operative connection.

15. The device as described in claim 1, wherein said detecting means comprises sampling means for periodically sampling the current produced by said source when substantially short circuited.

16. An end-of-life circuit in combination with a lithium type source having a resistance-use characteristic comprising a first portion which increases linearly with source usage followed by a knee portion after which the resistance increases sharply with usage, said circuit having means for determining when said source has reached said knee portion and for providing an end-of-life signal indicating that said source has reached said knee.

17. The circuit as described in claim 16, wherein said end-of-life signal is a first logic level before source usage is such that said knee has been reached, and a second logic level after said knee has been reached.

18. The circuit as described in claim 16, wherein said circuit comprises means for sampling an output variable of said source during a predetermined sampling period.

19. The circuit as described in claim 18, wherein said circuit comprises means for connecting said source to a load, and further means for isolating said load from said source and said circuit during said sampling period.

20. An electrical device in combination with and powered by a lithium-type source having an internal resistance which varies with source usage, said internal resistance comprising a first portion which increases substantially linearly with usage and a second portion which is substantially negligible until a certain usage after which it increases sharply, said device comprising circuit means for determining when said second internal resistance portion has increased following said certain usage.

21. The device as described in claim 20, wherein said circuit means determines when said second internal resistance portion has increased to at least a predetermined level.

22. The device as described in claim 21, wherein said circuit means comprises means for deriving a signal representative only of said second portion of said source internal resistance.

23. A detection circuit for detecting end of life of a lithium type source, said source having an effective electrolyte capacitor and resistance in parallel, and an effective depletion resistance, comprising
sampling means for placing a substantial short circuit across said source for a sampling period smaller than the time constant of said electrolyte capacitor and resistance in parallel so that the electrolyte capacitor within said source is effectively shunted and said source provides a short circuit current;
signal means for generating a current signal representative of said short circuit current and thus of source depletion resistance; and
comparing means for comparing said current signal with a predetermined reference and generating an end-of-life signal when the comparison indicates that the depletion resistance has reached a predetermined level.

24. The detection circuit as described in claim 23, wherein said sampling means comprises means for periodically placing said substantial short circuit across said source for said sampling period, whereby said detection circuit periodically performs said comparing.

25. The detection circuit as described in claim 23, comprising power enabling means for enabling said detection circuit after a certain usage of said source.

26. The detection circuit as described in claim 23, in combination with said source and a load circuit powered by said source, and comprising switching means in operative combination with said sampling means for alternately switching said load circuit and said detection circuit across said source.

27. The detection circuit as described in claim 23, wherein said sampling means comprises a current mirror circuit having an input placed across said source during said sampling period, and an output that provides a current substantially the same as the current into said input.

28. A cardiac pacer with a battery life detection circuit, comprising:
a. a battery source having an electrical characteristic represented by an open circuit voltage source and an impedance, said impedance having at least first and second resistance components, said first component having a linearly increasing value with source usage and being in combination with an effective electrolyte capacitance, said second component having a value which is negligible until it increases sharply after a certain source usage;

b. a stimulus generating circuit powered by said source for generating stimulus signals;

c. battery life circuit means in interfacing connection with said source for determining when said second component has increased from said negligible value to at least a predetermined higher value.

29. The pacer as described in claim 28, wherein said battery life circuit means comprises control means for generating a control signal as a function of said determining, said control means being in operative connection with said stimulus generating circuit for changing a parameter of said generated stimulus signals upon said determining.

30. The pacer as described in claim 28, wherein said source is a lithium iodine battery, said first resistance component of said battery being caused by the buildup of electrolyte in said cell, and said second resistance component being caused by the depletion of iodine in the cathode.

31. The pacer as described in claim 30, wherein said battery life circuit means comprises means for measuring an output variable of said battery for a time duration which is limited so that said effective capacitance is an effective short circuit for such time duration, whereby said measured variable is reflective substantially only of the non-linear component of said battery internal resistance.

32. The pacer as described in claim 31, wherein said battery life circuit means comprises substantially the only load on said source during said time duration.

33. The pacer as described in claim 32, wherein said battery life circuit means measures source current during said time duration.

34. The pacer as described in claim 32, wherein said battery life circuit means measures source voltage during said time duration.

35. The pacer as described in claim 32, wherein said time duration is on the order of 1 us.

36. The pacer as described in claim 28, wherein said battery life circuit is in operative combination with switching means for switching said source solely to said circuit for a time period limited so that said electrolyte capacitance is an effective short circuit during said time period.

37. The pacer as described in claim 36, wherein said battery life circuit has means for delivering a high frequency signal across said source, and for measuring said second source resistance component in terms of said delivered signal.

38. Apparatus for automatically monitoring the life of a lithium type battery source having an electrical characteristic represented by an open circuit voltage source and an impedance, said impedance having at least first and second resistance components, said first component having a linearly increasing value with source usage and being in combination with an effective electrolyte capacitance, said second component having a value which is negligible until it increases sharply after a certain source usage, comprising detector circuit means adapted to be connected across the output of said source and having sampling means for placing said detector circuit means into electrical contact with said source for a sampling period of $10^{-5}$ seconds or less and for generating a signal indicative of current flow from said source during said sampling period, and means for determining when said signal reaches a predetermined level.

39. The apparatus as described in claim 38, wherein said detector circuit means comprises a generator circuit for generating and delivering current to said source, and an indicator circuit for generating a signal indicative of said delivered current during said sampling period.

40. The apparatus as described in claim 38, wherein said sampling means comprises a CMOS inverter pair.

* * * * *

UNITED STATES PATENT AND TRADEMARK OFFICE
CERTIFICATE OF CORRECTION

PATENT NO. : 4,259,639
DATED : March 31, 1981
INVENTOR(S) : Alexis C. M. Renirie It is certified that error appears in the above-identified patent and that said Letters Patent are hereby corrected as shown below:

Column 1, line 43, change "withou" to --without--.

Column 3, line 23, change "correspondingly" to --corresponding--.

Column 3, line 39, change "circitry" to --circuitry--.

Column 5, line 65, after "through" insert --as though--.

Column 7, line 41, change "opration" to --operation--.

Column 8, line 7, change "mnodes" to --nodes--.

Signed and Sealed this

Seventh Day of July 1981

[SEAL]

Attest:

RENE D. TEGTMEYER

Attesting Officer     Acting Commissioner of Patents and Trademarks

UNITED STATES PATENT AND TRADEMARK OFFICE
CERTIFICATE OF CORRECTION

PATENT NO. : 4,259,639
DATED : March 31, 1981
INVENTOR(S) : Alexis C. M. Renirie It is certified that error appears in the above—identified patent and that said Letters Patent is hereby corrected as shown below:

Column 8, line 49, "U.S. Pat. No. 4,120,031" should read -- U.S. Pat. No. 4,124,031 --.

Signed and Sealed this

Eighteenth Day of August 1981

[SEAL]

Attest:

Attesting Officer

GERALD J. MOSSINGHOFF

Commissioner of Patents and Trademarks